(12) United States Patent
Divino et al.

(10) Patent No.: US 12,357,316 B2
(45) Date of Patent: Jul. 15, 2025

(54) IMPLANT DETACHMENT WITH THERMAL ACTIVATION

(71) Applicant: Covidien LP, Mansfield, MA (US)

(72) Inventors: Vincent Divino, Mission Viejo, CA (US); Richard Rhee, Anaheim Hills, CA (US)

(73) Assignee: Covidien LP, Mansfield, MA (US)

( * ) Notice: Subject to any disclaimer, the term of this patent is extended or adjusted under 35 U.S.C. 154(b) by 853 days.

(21) Appl. No.: 17/303,869

(22) Filed: Jun. 9, 2021

(65) Prior Publication Data

US 2021/0290246 A1 Sep. 23, 2021

Related U.S. Application Data

(62) Division of application No. 15/610,713, filed on Jun. 1, 2017, now Pat. No. 11,051,822.

(60) Provisional application No. 62/355,431, filed on Jun. 28, 2016.

(51) Int. Cl.
*A61B 17/12* (2006.01)
*A61B 17/00* (2006.01)
*A61M 29/02* (2006.01)

(52) U.S. Cl.
CPC .... *A61B 17/12113* (2013.01); *A61B 17/0057* (2013.01); *A61B 17/12031* (2013.01); *A61M 29/02* (2013.01); *A61B 2017/00632* (2013.01); *A61B 2017/00862* (2013.01); *A61B 2017/00867* (2013.01); *A61B 2017/00955* (2013.01); *A61B 2017/12054* (2013.01);
(Continued)

(58) Field of Classification Search
CPC .......... A61B 17/12113; A61B 17/0057; A61B 17/12031; A61B 17/1214; A61B 17/12168; A61B 2017/12054; A61B 2017/12077; A61B 2017/12068; A61B 2017/1209; A61B 2017/00632; A61B 2017/00862; A61B 2017/00867; A61B 2017/00955
See application file for complete search history.

(56) References Cited

U.S. PATENT DOCUMENTS

| 5,108,407 A | 4/1992 | Geremia et al. |
| 5,122,136 A | 6/1992 | Guglielmi et al. |
| 5,250,071 A | 10/1993 | Palermo |

(Continued)

FOREIGN PATENT DOCUMENTS

| DE | 4445715 A1 | 6/1996 |
| EP | 1884208 A1 | 2/2008 |

(Continued)

*Primary Examiner* — Katherine M Rodjom
(74) *Attorney, Agent, or Firm* — Fortem IP LLP

(57) ABSTRACT

Treatment of an aneurysm or other vascular defect can be facilitated or enhanced by an implant delivered with a thermally activated detachment system. A delivery system can include an implant with a proximal portion that defines a port. A pusher device can include arms extending distally from a junction of the pusher device and through the port, with distal sections of the arms disposed within the implant. The arms can, at a certain temperature, transition from engagement with the implant to a shape that facilitates release of the implant. Additionally or alternatively, a coil can engage an outer surface of the implant at the proximal portion and transition to a shape that facilitates release of the implant.

16 Claims, 10 Drawing Sheets

(52) U.S. Cl.
CPC . *A61B 2017/12077* (2013.01); *A61B 17/1214* (2013.01); *A61B 17/12172* (2013.01)

(56) References Cited

U.S. PATENT DOCUMENTS

| | | | |
|---|---|---|---|
| 5,354,295 A | 10/1994 | Guglielmi et al. | |
| 5,370,653 A | 12/1994 | Cragg | |
| 5,423,829 A | 6/1995 | Pham et al. | |
| 5,509,411 A | 4/1996 | Littmann et al. | |
| 5,522,836 A | 6/1996 | Palermo | |
| 5,540,680 A | 7/1996 | Guglielmi et al. | |
| 5,624,449 A | 4/1997 | Pham et al. | |
| 5,658,308 A | 8/1997 | Snyder | |
| 5,669,931 A | 9/1997 | Kupiecki et al. | |
| 5,690,667 A | 11/1997 | Gia | |
| 5,733,329 A | 3/1998 | Wallace et al. | |
| 5,743,905 A | 4/1998 | Eder et al. | |
| 5,749,894 A | 5/1998 | Engelson | |
| 5,766,629 A | 6/1998 | Cho et al. | |
| 5,800,455 A | 9/1998 | Palermo et al. | |
| 5,851,206 A | 12/1998 | Guglielmi et al. | |
| 5,853,418 A | 12/1998 | Ken et al. | |
| 5,855,578 A | 1/1999 | Guglielmi et al. | |
| 5,891,128 A | 4/1999 | Gia et al. | |
| 5,895,385 A | 4/1999 | Guglielmi et al. | |
| 5,916,235 A | 6/1999 | Guglielmi | |
| 5,919,187 A | 7/1999 | Guglielmi et al. | |
| 5,925,037 A | 7/1999 | Guglielmi et al. | |
| 5,925,059 A | 7/1999 | Palermo et al. | |
| 5,928,226 A | 7/1999 | Guglielmi et al. | |
| 5,935,145 A | 8/1999 | Villar et al. | |
| 5,941,888 A | 8/1999 | Wallace et al. | |
| 5,944,114 A | 8/1999 | Farley | |
| 5,947,962 A | 9/1999 | Guglielmi et al. | |
| 5,947,963 A | 9/1999 | Guglielmi | |
| 5,951,599 A | 9/1999 | McCrory | |
| 5,964,797 A | 10/1999 | Ho | |
| 5,976,126 A | 11/1999 | Guglielmi | |
| 5,984,929 A | 11/1999 | Bashiri et al. | |
| 6,010,498 A | 1/2000 | Guglielmi | |
| 6,013,084 A | 1/2000 | Ken et al. | |
| 6,059,779 A | 5/2000 | Mills | |
| 6,063,070 A | 5/2000 | Eder | |
| 6,063,104 A | 5/2000 | Villar et al. | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,123,714 A | 9/2000 | Gia et al. | |
| 6,136,015 A | 10/2000 | Kurz et al. | |
| 6,146,373 A | 11/2000 | Cragg et al. | |
| 6,156,061 A | 12/2000 | Wallace et al. | |
| 6,165,178 A | 12/2000 | Bashiri et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,193,728 B1 | 2/2001 | Ken et al. | |
| 6,238,403 B1 | 5/2001 | Greene et al. | |
| 6,241,691 B1 | 6/2001 | Ferrera et al. | |
| 6,280,457 B1 | 8/2001 | Wallace et al. | |
| 6,296,622 B1 | 10/2001 | Kurz et al. | |
| 6,299,619 B1 | 10/2001 | Greene et al. | |
| 6,306,153 B1 | 10/2001 | Kurz et al. | |
| 6,309,367 B1 | 10/2001 | Boock | |
| 6,371,972 B1 | 4/2002 | Wallace et al. | |
| 6,409,721 B1 | 6/2002 | Wheelock et al. | |
| 6,416,373 B1 | 7/2002 | Kolb et al. | |
| 6,425,893 B1 | 7/2002 | Guglielmi | |
| 6,425,914 B1 | 7/2002 | Wallace et al. | |
| 6,468,266 B1 | 10/2002 | Bashiri et al. | |
| 6,468,301 B1 | 10/2002 | Amplatz et al. | |
| 6,478,773 B1 * | 11/2002 | Gandhi ............ | A61B 17/12136 604/113 |
| 6,485,524 B2 | 11/2002 | Strecker | |
| 6,486,266 B2 | 11/2002 | Amano et al. | |
| 6,511,468 B1 | 1/2003 | Cragg et al. | |
| 6,533,801 B2 | 3/2003 | Wallace et al. | |
| 6,558,367 B1 | 5/2003 | Cragg et al. | |
| 6,589,230 B2 | 7/2003 | Gia et al. | |
| 6,589,236 B2 | 7/2003 | Wheelock et al. | |
| 6,602,261 B2 | 8/2003 | Greene et al. | |
| 6,605,101 B1 | 8/2003 | Schaefer et al. | |
| 6,620,152 B2 | 9/2003 | Guglielmi | |
| 6,623,493 B2 | 9/2003 | Wallace et al. | |
| 6,723,112 B2 | 4/2004 | Ho et al. | |
| 6,743,251 B1 | 6/2004 | Eder | |
| 6,835,185 B2 | 12/2004 | Ramzipoor et al. | |
| 6,878,384 B2 | 4/2005 | Cruise et al. | |
| 6,905,503 B2 | 6/2005 | Gifford et al. | |
| 6,936,055 B1 | 8/2005 | Ken et al. | |
| 6,953,473 B2 | 10/2005 | Porter | |
| 6,964,657 B2 | 11/2005 | Cragg et al. | |
| 6,966,892 B2 | 11/2005 | Gandhi et al. | |
| 7,014,645 B2 | 3/2006 | Greene et al. | |
| 7,083,567 B2 | 8/2006 | Mawad | |
| 7,128,736 B1 | 10/2006 | Abrams et al. | |
| 7,166,122 B2 | 1/2007 | Aganon et al. | |
| 7,169,172 B2 | 1/2007 | Levine et al. | |
| 7,198,613 B2 | 4/2007 | Gandhi et al. | |
| 7,229,461 B2 | 6/2007 | Chin et al. | |
| 7,238,194 B2 | 7/2007 | Monstadt et al. | |
| 7,255,707 B2 | 8/2007 | Ramzipoor et al. | |
| 7,300,458 B2 | 11/2007 | Henkes et al. | |
| 7,323,000 B2 | 1/2008 | Monstdt et al. | |
| 7,331,974 B2 | 2/2008 | Schaefer et al. | |
| 7,485,122 B2 | 2/2009 | Teoh | |
| 7,524,322 B2 | 4/2009 | Monstadt et al. | |
| 7,601,160 B2 | 10/2009 | Richter | |
| 7,608,089 B2 | 10/2009 | Wallace et al. | |
| RE41,029 E | 12/2009 | Guglielmi et al. | |
| 7,651,513 B2 | 1/2010 | Teoh et al. | |
| 7,695,484 B2 | 4/2010 | Wallace et al. | |
| 7,879,064 B2 | 2/2011 | Monstadt et al. | |
| 7,896,899 B2 | 3/2011 | Patterson et al. | |
| 7,938,845 B2 | 5/2011 | Aganon et al. | |
| RE42,625 E | 8/2011 | Guglielmi | |
| 8,002,789 B2 | 8/2011 | Ramzipoor et al. | |
| RE42,756 E | 9/2011 | Guglielmi et al. | |
| 8,016,869 B2 | 9/2011 | Nikolchev | |
| 8,021,416 B2 | 9/2011 | Abrams | |
| 8,043,326 B2 | 10/2011 | Hancock et al. | |
| 8,048,104 B2 | 11/2011 | Monstadt et al. | |
| RE43,311 E | 4/2012 | Wallace et al. | |
| 8,157,855 B2 | 4/2012 | Eidenschink et al. | |
| 8,202,292 B2 | 6/2012 | Kellett | |
| 8,221,396 B2 | 7/2012 | Dehnad et al. | |
| 8,221,483 B2 | 7/2012 | Ford et al. | |
| 8,273,116 B2 | 9/2012 | Licata et al. | |
| 8,298,256 B2 | 10/2012 | Gandhi et al. | |
| 8,328,860 B2 | 12/2012 | Strauss et al. | |
| 8,372,110 B2 | 2/2013 | Monstadt et al. | |
| 8,398,671 B2 | 3/2013 | Chen et al. | |
| 8,425,541 B2 | 4/2013 | Masters et al. | |
| 8,470,013 B2 | 6/2013 | Duggal et al. | |
| 8,480,701 B2 | 7/2013 | Monstadt | |
| 8,562,667 B2 | 10/2013 | Cox | |
| 8,597,321 B2 | 12/2013 | Monstadt et al. | |
| 8,632,584 B2 | 1/2014 | Henkes et al. | |
| 8,641,746 B2 | 2/2014 | Andreas et al. | |
| 8,641,777 B2 | 2/2014 | Strauss et al. | |
| 8,652,163 B2 | 2/2014 | Padilla et al. | |
| 8,657,870 B2 | 2/2014 | Turovskiy et al. | |
| 8,715,312 B2 | 5/2014 | Burke et al. | |
| 8,715,317 B1 | 5/2014 | Janardhan et al. | |
| 8,721,625 B2 | 5/2014 | Klint | |
| 8,728,142 B2 | 5/2014 | Gandhi et al. | |
| 8,777,978 B2 | 7/2014 | Strauss et al. | |
| 8,777,979 B2 | 7/2014 | Shrivastava et al. | |
| 8,795,320 B2 | 8/2014 | Strauss et al. | |
| 8,795,321 B2 | 8/2014 | Strauss et al. | |
| 8,801,747 B2 | 8/2014 | Strauss et al. | |
| 8,845,676 B2 | 9/2014 | Monstadt et al. | |
| 8,864,790 B2 | 10/2014 | Strauss et al. | |
| 8,870,909 B2 | 10/2014 | Cox | |
| 8,876,863 B2 | 11/2014 | Eskridge | |

(56) References Cited

U.S. PATENT DOCUMENTS

| | | |
|---|---|---|
| 8,900,285 B2 | 12/2014 | Licata |
| 8,906,057 B2 | 12/2014 | Connor et al. |
| 8,915,950 B2 | 12/2014 | Cam et al. |
| 8,926,681 B2 | 1/2015 | Levy et al. |
| 8,932,317 B2 | 1/2015 | Marks et al. |
| 8,940,011 B2 | 1/2015 | Teoh et al. |
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeger et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 11,051,822 B2 | 7/2021 | Divino et al. |
| 2001/0000797 A1 | 5/2001 | Mazzocchi |
| 2001/0001835 A1 | 5/2001 | Greene et al. |
| 2002/0151883 A1 | 10/2002 | Guglielmi |
| 2003/0014073 A1 | 1/2003 | Bashiri et al. |
| 2003/0018294 A1 | 1/2003 | Cox |
| 2003/0028209 A1 | 2/2003 | Teoh et al. |
| 2003/0040733 A1 | 2/2003 | Cragg et al. |
| 2003/0040772 A1 | 2/2003 | Hyodoh et al. |
| 2003/0060833 A1 | 3/2003 | Carrison et al. |
| 2003/0176857 A1 | 9/2003 | Lee |
| 2003/0212426 A1 | 11/2003 | Olson et al. |
| 2003/0225365 A1 | 12/2003 | Greff et al. |
| 2004/0002731 A1 | 1/2004 | Aganon et al. |
| 2004/0225279 A1 | 11/2004 | Raymond |
| 2004/0236344 A1 | 11/2004 | Monstadt et al. |
| 2005/0079196 A1 | 4/2005 | Henkes et al. |
| 2005/0267511 A1 | 12/2005 | Marks et al. |
| 2006/0036281 A1 | 2/2006 | Patterson et al. |
| 2006/0100602 A1 | 5/2006 | Klint |
| 2006/0135986 A1 | 6/2006 | Wallace et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0271097 A1 | 11/2006 | Ramzipoor et al. |
| 2007/0073334 A1 | 3/2007 | Ramzipoor |
| 2007/0100426 A1 | 5/2007 | Rudakov et al. |
| 2007/0175536 A1 | 8/2007 | Monetti et al. |
| 2007/0186933 A1* | 8/2007 | Domingo ......... A61B 17/12104 606/205 |
| 2007/0191924 A1 | 8/2007 | Rudakov |
| 2008/0045922 A1 | 2/2008 | Cragg et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0076540 A1* | 3/2009 | Marks ............ A61B 17/12145 606/200 |
| 2009/0143786 A1 | 6/2009 | Bashiri et al. |
| 2009/0227976 A1 | 9/2009 | Calabria et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0144895 A1 | 6/2010 | Porter |
| 2010/0256666 A1 | 10/2010 | Chen et al. |
| 2010/0268204 A1 | 10/2010 | Tieu et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0137405 A1 | 6/2011 | Wilson et al. |
| 2011/0184453 A1 | 7/2011 | Levy et al. |
| 2012/0010648 A1 | 1/2012 | Monstadt et al. |
| 2012/0209310 A1 | 8/2012 | Chen et al. |
| 2012/0271344 A1 | 10/2012 | Ford et al. |
| 2012/0316632 A1 | 12/2012 | Gao |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2013/0274866 A1 | 10/2013 | Cox et al. |
| 2014/0005651 A1 | 1/2014 | Eskridge |
| 2014/0012307 A1 | 1/2014 | Franano et al. |
| 2014/0039535 A1 | 2/2014 | Eskuri |
| 2014/0058420 A1 | 2/2014 | Hannes et al. |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0316012 A1 | 10/2014 | Freyman et al. |
| 2014/0371734 A1 | 12/2014 | Truckai |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |
| 2015/0216684 A1 | 8/2015 | Enzmann et al. |
| 2015/0250628 A1 | 9/2015 | Monstadt et al. |
| 2015/0272589 A1* | 10/2015 | Lorenzo ......... A61B 17/12145 606/200 |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |

FOREIGN PATENT DOCUMENTS

| | | |
|---|---|---|
| EP | 2668914 A1 | 12/2013 |
| WO | 2011066962 A1 | 6/2011 |
| WO | 2014078286 A1 | 5/2014 |
| WO | 2017074411 A1 | 5/2017 |
| WO | 2018051187 A1 | 3/2018 |

* cited by examiner

IMPLANT DETACHMENT WITH THERMAL ACTIVATION

CROSS-REFERENCE TO RELATED APPLICATIONS

This application is a divisional of U.S. application Ser. No. 15/610,713, filed Jun. 1, 2017, which claims the benefit of priority of U.S. Provisional Patent Application No. 62/355,431, filed Jun. 28, 2016, both of which are hereby incorporated by reference in their entirety.

FIELD

The subject technology relates to the delivery of implantable medical devices and systems for delivering implantable medical devices.

BACKGROUND

The use of endovascular techniques for the implantation of medical devices for treatment, e.g., by occlusion, of body cavities such as arteries, veins, fallopian tubes or vascular deformities is known in the art. For example, vascular aneurysms can be occluded with an implant that is introduced with a pusher member through a catheter. Once advanced to the treatment site, the implant is inserted into the aneurysm cavity to occlude the aneurysm and then detached from the pusher member.

SUMMARY

Detachment of an implant from the pusher member can be problematic. It is essential that the implant form as small a profile as possible to be guided through the fine bore of a catheter and it must be configured to bring about a reliable severance of the implant from the pusher member. Absent a reliable severance of the implant, withdrawal of the pusher member and catheter may cause unintended removal of the implant from the aneurysm or vessel to be occluded, and thus injure and/or rupture of the wall of the aneurysm or vessel.

A thermally activated detachment mechanism can be employed for controllably releasing an implantable medical device from a delivery connection assembly in a reliable, rapid, and accurate manner. Thermally activated detachment mechanisms can have advantages compared to electrolytic detachment systems. For example, severance of implantable medical devices can involve engagement and disengagement by a delivery connection assembly that minimizes a protruding aspect of the medical devices at an engagement region thereof. The delivery connection assembly can be designed to engage the medical device such that, after disengagement, the mechanisms for engagement are removed with the delivery connection assembly. Such an arrangement can facilitate rapid severance and leave a medical device without an end that protrudes as far as would an implant's connection to an electrolytic detachment junction after detachment.

In contrast, electrolytic detachment of an implant can leave a portion of the delivery wire protruding from the implant after detachment, presenting a risk of harm to the surrounding anatomy. Additionally, electrolytic detachment can leave behind debris, such as small particulate matter, that can interfere with MRI imaging during a procedure.

Thermally activated detachment mechanisms also can have advantages compared to mechanical detachment systems. For example, while some mechanical methods for the severance of implants from delivery systems are reliable, mechanical energy must be transmitted (e.g., by rotation of the delivery wire), which may cause the implant to be dislodged out of the correct position. A thermally activated detachment system can avoid the need for transmission of mechanical energy.

The subject technology is illustrated, for example, according to various aspects described below. Various examples of aspects of the subject technology are described as numbered clauses (1, 2, 3, etc.) for convenience. These are provided as examples and do not limit the subject technology.

Clause 1. A delivery system, comprising:
an implant comprising (i) a proximal portion that defines a port at a proximal end of the implant and having a port inner cross-sectional dimension and (ii) a cavity distal to the port and having a cavity inner cross-sectional dimension, larger than the port inner cross-sectional dimension; and
a pusher device comprising arms extending distally from a junction of the pusher device and through the port, with distal sections of the arms disposed within the cavity, the arms having a first configuration in which the distal sections are a first distance apart to define a first outer cross-sectional dimension, larger than the port inner cross-sectional dimension, the arms having a second configuration in which the distal sections are a second distance apart to define a second outer cross-sectional dimension, smaller than the port inner cross-sectional dimension, and the arms being configured to transition from the first configuration to the second configuration when above a transition temperature.

Clause 2. The delivery system of clause 1, wherein each of the arms comprises a longitudinal section extending from the junction to the distal section.

Clause 3. The delivery system of any one of clauses 1-2, wherein the distal sections extend radially outwardly.

Clause 4. The delivery system of any one of clauses 1-3, wherein the distal sections define a maximum outer cross-sectional dimension of a distal region of the pusher device.

Clause 5. The delivery system of any one of clauses 1-4, wherein the arms are of a shape memory material.

Clause 6. The delivery system of any one of clauses 1-5, further comprising a heating element thermally connected to the pusher device.

Clause 7. The delivery system of any one of clauses 1-6, further comprising an electrical circuit thermally connected to the pusher device.

Clause 8. The delivery system of any one of clauses 1-7, wherein the proximal portion of the implant is a circumferentially continuous hub.

Clause 9. The delivery system of any one of clauses 1-8, wherein the proximal portion of the implant is a helical coil.

Clause 10. A method of delivering an implant, the method comprising:
positioning the implant at a target location within a patient while the implant is attached to a pusher device, wherein the implant comprises (i) a proximal portion that defines a port at a proximal end of the implant and having a port inner cross-sectional dimension and (ii) a cavity distal to the port and having a cavity inner cross-sectional dimension, larger than the port inner cross-sectional dimension, wherein the pusher device comprises arms extending distally from a junction of the pusher device and through the port, with distal sections of the arms disposed within the cavity; and releasing the implant from the pusher device by increasing a temperature of the arms, such that the arms transition from (i) a first configuration in which the distal sections are a first distance apart to define a first outer cross-sectional dimension, larger than the port inner cross-sectional dimension to (ii) a second configuration in which the distal sections are a second distance apart to define a second outer cross-sectional dimension, smaller than the port inner cross-sectional dimension.

Clause 11. The method of clause 10, wherein the releasing comprises operating a heating element thermally connected to the pusher device.

Clause 12. The method of any one of clauses 10-11, wherein the releasing comprises conducting an electrical current through the pusher device.

Clause 13. The method of any one of clauses 10-12, wherein the releasing comprises retracting the distal sections of the arms proximally from the cavity through the port.

Clause 14. The method of clause 13, wherein the releasing further comprises, while retracting the distal sections of the arms, stabilizing the implant with a catheter housing at least a portion of the pusher device.

Clause 15. The method of any one of clauses 10-14, wherein the releasing comprises articulating the arms with respect to the junction.

Clause 16. A delivery system, comprising:
an implant comprising a proximal portion that defines an outer cross-sectional dimension; and
a pusher device comprising a coil extending helically about the proximal portion;
wherein the coil has a first configuration in which the coil is biased to form a lumen with a first inner cross-sectional dimension, smaller than the outer cross-sectional dimension of the proximal portion;
wherein the coil has a second configuration in which the lumen of the coil has a second inner cross-sectional dimension, larger than the outer cross-sectional dimension of the proximal portion;
wherein the coil is configured to transition from the first configuration to the second configuration when above a transition temperature.

Clause 17. The delivery system of clause 16, wherein at least a portion of the coil extends distally of an entire length of the proximal portion.

Clause 18. The delivery system of any one of clauses 16-17, wherein the coil is of a shape memory material.

Clause 19. The delivery system of any one of clauses 16-18, further comprising a heating element thermally connected to the pusher device.

Clause 20. The delivery system of any one of clauses 16-19, further comprising an electrical circuit thermally connected to the pusher device.

Clause 21. The delivery system of any one of clauses 16-20, wherein the proximal portion of the implant is a circumferentially continuous hub.

Clause 22. A method of delivering an implant, the method comprising:
positioning the implant at a target location within a patient while the implant is attached to a pusher device, wherein the implant comprises a proximal portion that defines an outer cross-sectional dimension, wherein the pusher device comprises a coil extending helically about the proximal portion; and
releasing the implant from the pusher device by increasing a temperature of the coil, such that the coil transitions from (i) a first configuration in which the coil is biased to form a lumen with a first inner cross-sectional dimension, smaller than the outer cross-sectional dimension of the proximal portion to (ii) a second configuration in which the lumen of the coil has a second inner cross-sectional dimension, larger than the outer cross-sectional dimension of the proximal portion.

Clause 23. The method of clause 22, wherein the releasing comprises operating a heating element thermally connected to the pusher device.

Clause 24. The method of any one of clauses 22-23, wherein the releasing comprises conducting an electrical current through the coil.

Clause 25. The method of any one of clauses 22-24, wherein the releasing comprises retracting the coil proximally from the implant.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplifying and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. In some instances, well-known structures and components are shown in block diagram form in order to avoid obscuring the concepts of the subject technology.

Figure 1A:
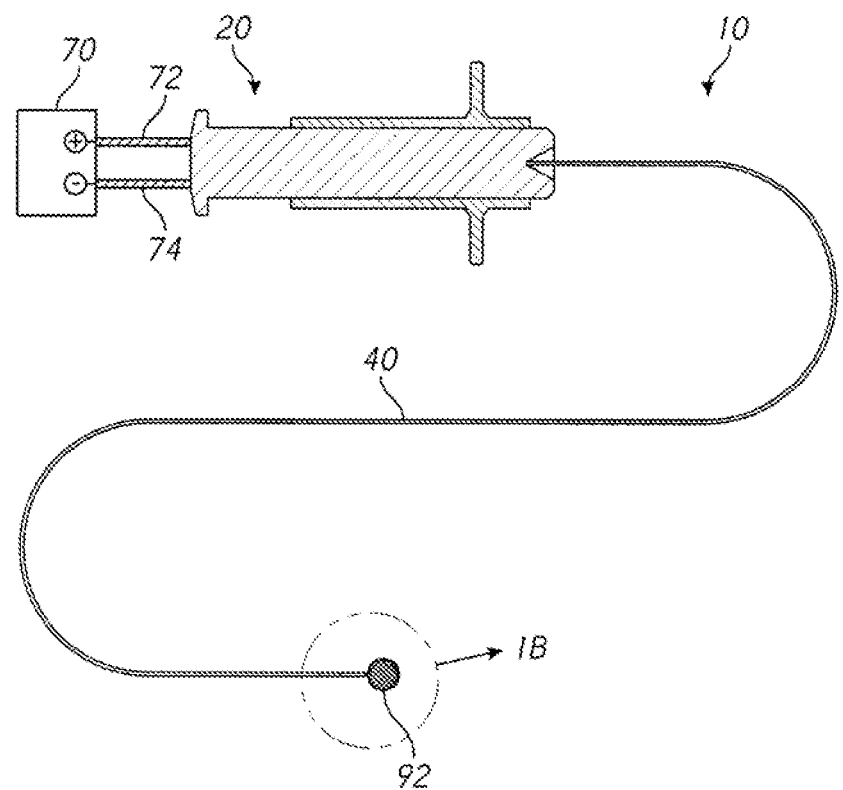
FIG. 1A shows a plan view of a delivery system in accordance with some embodiments of the subject technology.
Figure 1B:
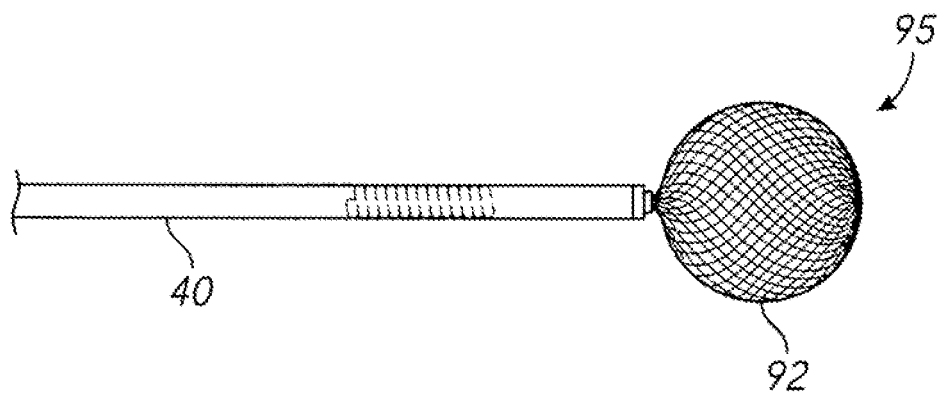
FIG. 1B shows an enlarged view of a distal portion of FIG. 1A, in accordance with one or more embodiments of the present disclosure.

An implantable medical device, e.g., a vascular implant, may be positioned using a delivery system 10 such as, for example, the one shown in FIGS. 1A-1B. As illustrated in FIGS. 1A-1B for example, the delivery system 10 can include an actuator 20, a positioner 40 coupled with the actuator 20, and a delivery connection assembly (not shown) extending from the actuator 20 and within the positioner 40. A portion of a delivery system 10 may engage a complementary portion of an implant 95 in order to control the delivery and detachment of the implant 95 at the desired location.

A power supply 70 can be coupled to a proximal portion of the positioner 40, for example at the actuator 20. A current can flow from the power supply 70 along a first lead 72 to a location near the implant 95 and along a second lead 74 from the location near the implant 95 to the power supply 70. The power supply 70 may be a direct current power supply, an alternating current power supply, or a power supply switchable between a direct current and an alternating current. A positive terminal of the power supply 70, for example as shown in FIG. 1A, may be coupled to the first lead 72, and a negative terminal of the power supply 70 may be coupled to the second lead 74. The power supply 70 may provide a current through the delivery system 10 to initiate a heating process during use of the delivery system 10 to release the implant 95, as discussed further herein. According to some embodiments, the power supply 70 can include an electrical generator configured to output an electrical current that is sufficient to actuate the delivery system 10 to release the implant 95. The power supply 70 can include a suitable controller that can be used to control various parameters of the energy output by the generator, such as intensity, amplitude, duration, frequency, duty cycle, and polarity.

Figure 2A:
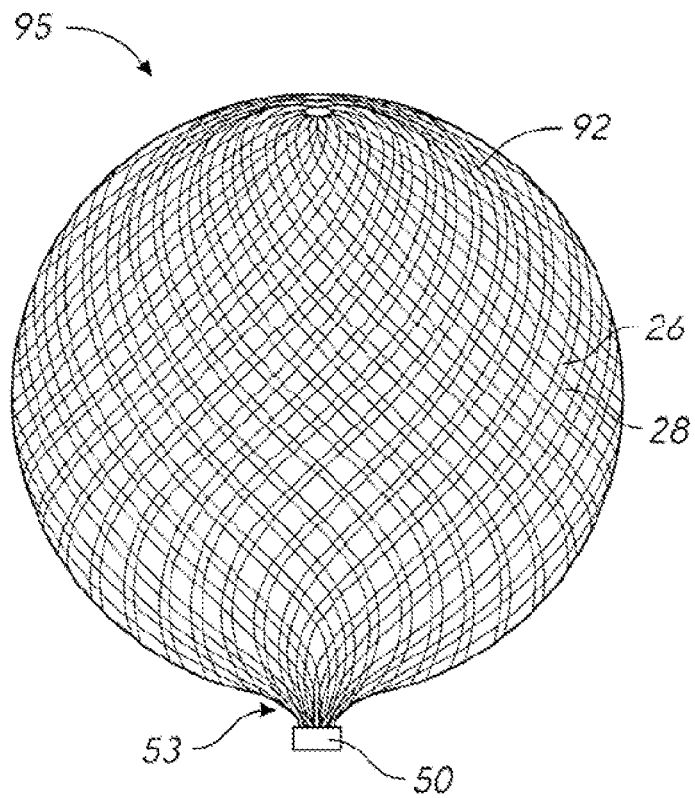
FIG. 2A shows a perspective side view of a braid ball implant, in accordance with one or more embodiments of the subject technology.
Figure 2B:
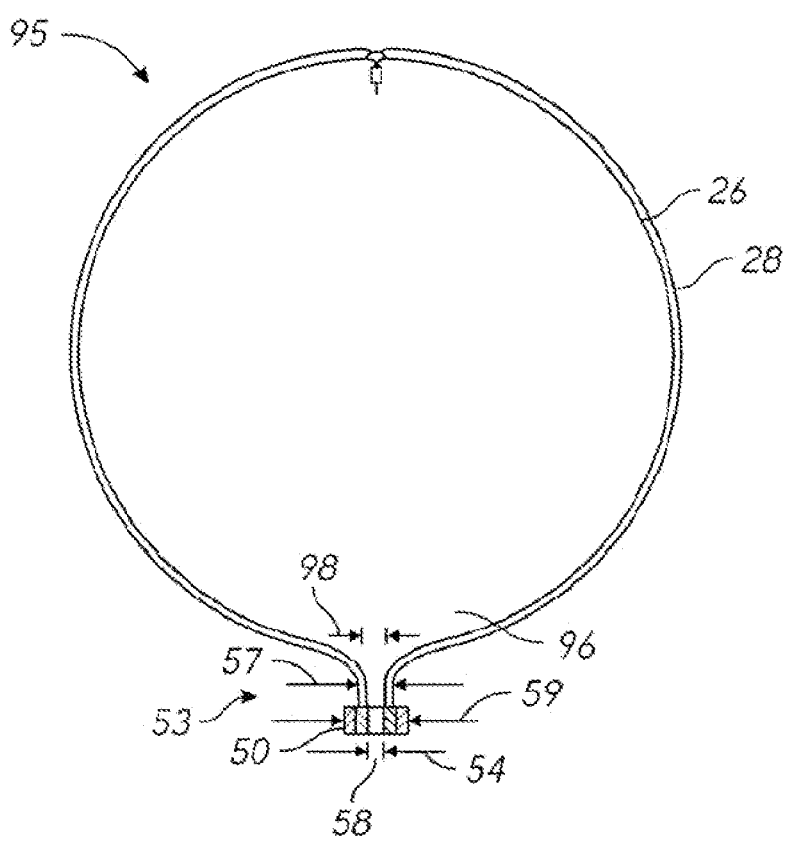
FIG. 2B shows a sectional view of the braid ball implant of FIG. 2B, in accordance with one or more embodiments of the subject technology.

According to some embodiments, for example as shown in FIGS. 2A-2B, an implant 95 delivered by the delivery system 10 can be or include a braid ball 92. While the implant 95 is shown or described in several embodiments as comprising a braid ball 92, any implant or device that is compatible with the subject technology may be used in lieu of or in conjunction with the example implant 95 disclosed herein, in accordance with the embodiments described herein. Suitable implants and devices include, but are not limited to, stents, filters, thrombectomy devices, atherectomy devices, flow restoration devices, embolic coils, spherical devices, embolic protection devices, or other well-known treatment devices.

The braid ball 92 can be formed from tubular braid stock including a resilient material, such as nitinol, that defines an open volume in an uncompressed/unconstrained state. The size of the implant can be selected to fill an aneurysm when expanded therein. The implant 95 can include a hub 50 and layers 26, 28. The hub can be located at a proximal portion 53 of the implant. The hub 50 can be fixedly attached to the remainder of the implant 95. For example, the hub 50 can grasp braided filaments of the layers 26, 28 of the implant 95. The implant 95 can include the layers 26, 28 at least where impacted by flow at a neck of the aneurysm.

Figure 3:
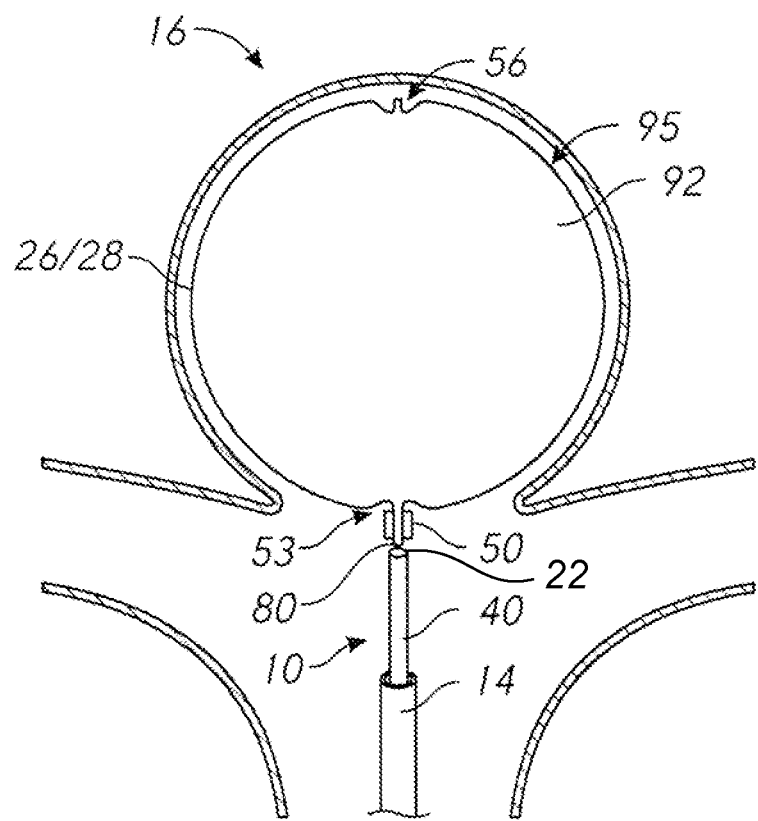
FIG. 3 shows in partial cross-section a portion of the delivery system and the braid ball implant of FIGS. 2A-2B, in accordance with some embodiments of the subject technology.

According to some embodiments, the hub 50 can be fixedly attached to the remainder of the implant 95. For example, the hub 50 can grasp braided filaments of the layers 26, 28 of the implant 95. A port 54 can be provided within the hub 50. The port 54 can define a port inner cross-sectional dimension 58. The port inner cross-sectional dimension 58 can be a minimum or maximum inner cross-sectional dimension within a region of the proximal portion 53. For example, a region distal to the hub 50 can include a cavity 96 that defines an inner cross-sectional dimension 98 that is greater than the port inner cross-sectional dimension 58. The hub 50 can further define a hub outer cross-sectional dimension 59. The hub outer cross-sectional dimension 59 can be a minimum or maximum outer cross-sectional dimension within a region of the proximal portion 53. For example, a region distal to the hub 50 can define an outer cross-sectional dimension 57 that is smaller than the hub outer cross-sectional dimension 59. The port 54 or an outer surface of the hub 50 can accept the implant 95. Delivery system construction and further optional details of the implant 95 are provided below. FIG. 3 shows the braid ball 92 attached to a distal end 22 of the delivery system 10, and positioned within an aneurysm 16. The delivery system 10 extends proximally from the implant 95 to a location outside of the body where the delivery system can be manipulated by a user. As illustrated in FIG. 3, the delivery system 10 can comprise a microcatheter 14 and a delivery connection assembly that includes the positioner 40. The microcatheter 14 is advanced until its distal end is in the vicinity of a target site, such as the aneurysm 16, for example as shown in FIG. 3. The positioner 40 is advanced within the microcatheter 14 to access the target site. The positioner 40 can be advanced out of the microcatheter 14 and directed to the target site. The implant 95 can be advanced with the positioner 40 until the implant 95 is positioned at the target site.

The delivery system 10 and the microcatheter 14 can have lengths sufficient to extend from outside the patient's body to a target location in the brain. For example, each of them can be at least 125 cm long, and more particularly may be between about 125 cm and about 175 cm long, with the delivery system 10 being longer than the microcatheter 14. Typically the microcatheter 14 is about 155 cm long. Commercially available microcatheters which may be suitable for use as delivery catheters include the REBAR™ Reinforced Micro Catheter, which is available from Medtronic, Inc. and the MARKSMAN™ Catheter, which is available from Medtronic, Inc.

When the delivery system 10 has been advanced to a target aneurysm 16, the implant 95 can be inserted within the aneurysm 16 and expanded to a fully deployed state, for example as illustrated in FIG. 3. The position of the implant 95 can be affected and/or modified by corresponding motion of the delivery system 10. A radiopaque marker (e.g., the hub 50) of the implant 95 can be utilized to track and confirm delivery of the implant 95 to the target location.

Figure 4:
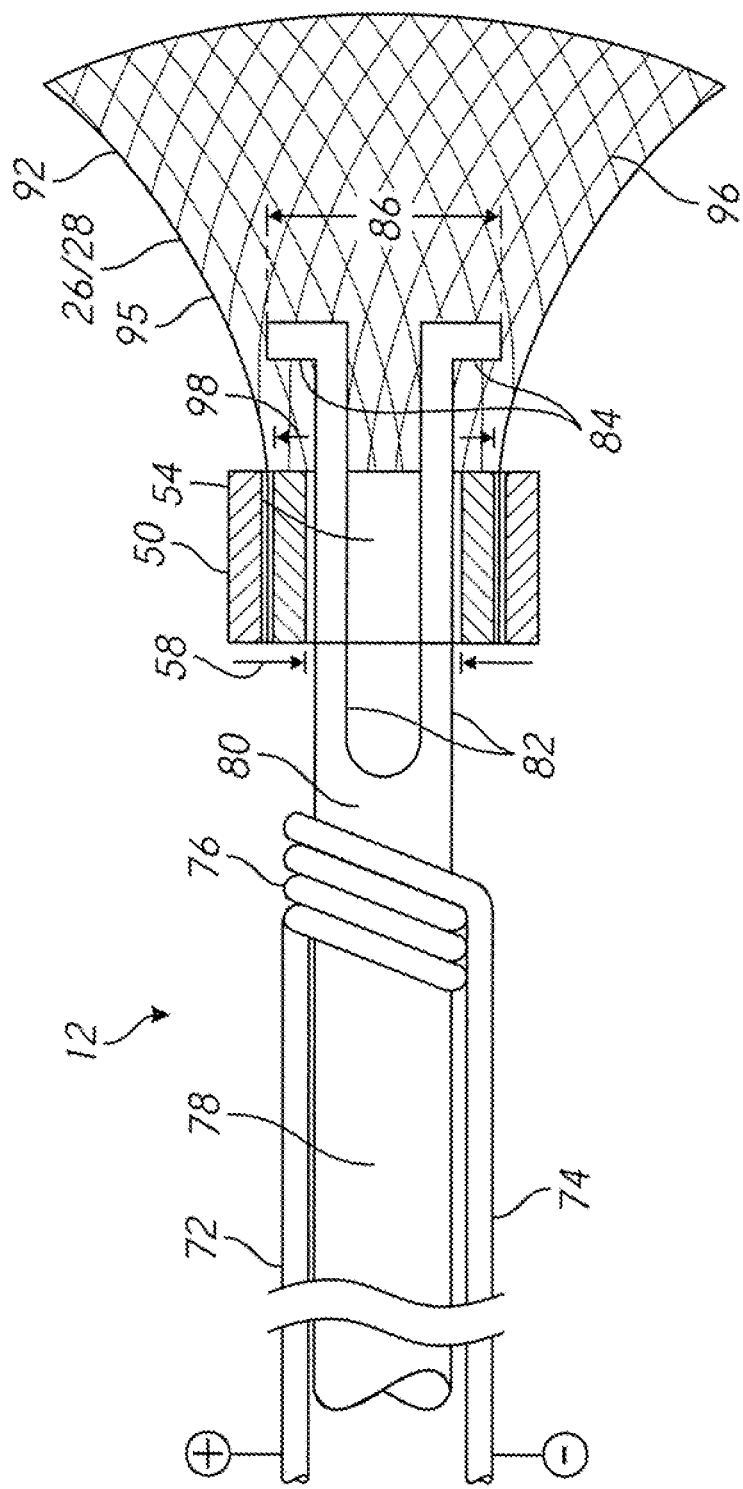
FIG. 4 shows a partial sectional view of a distal end of the delivery system of FIG. 1A connected to a proximal portion of the braid ball implant of FIGS. 2A-2B, in accordance with one or more embodiments of the subject technology.

According to some embodiments, the implant 95 is supported during delivery by a delivery connection assembly 12, from which the implant 95 can also be detached. According to some embodiments, for example as shown in FIG. 4, the delivery connection assembly 12 can include the positioner 40, a pusher device 78 and a heating element 76. The pusher device 78 can include one or more arms 82 that engage the implant 95. The heating element 76 can controllably provide heat to the pusher device 78 to actuate the arms until the arms 82 released the implant 95.

According to some embodiments, the pusher device 78 can include one or more arms 82 extending distally from a junction 80 of the pusher device 78 and through the port 54. One or more of the arms 82 can include a distal section 84 that can be positioned distal to at least a portion of the port 54 and/or within a cavity 96 of the implant 95. According to some embodiments, the arms 82 can extend longitudinally from the junction 80, and the distal sections 84 can extend radially outwardly from the arms 82. In at least one configuration, the distal sections 84 can define a maximum outer cross-sectional dimension 86 that is greater than the port inner cross-sectional dimension 58. Accordingly, passage of the distal sections 84 proximally through the port 54 is resisted until the distal sections 84 are transitioned to a different configuration.

According to some embodiments, the arms 82 are configured to flex, bend, pivot, or articulate with respect to the junction 80 in response to temperature changes. Such action can be achieved based on a programmed characteristic of the arms 82. When the arms 82 are at or above a transition temperature, the arms 82 can transition to a second configuration, such as an austenite state in a shape memory alloy, in which the arms 82 in a relaxed state can disengage from the implant 95, as will be more fully described herein.

The transition temperature at which the arms 82 begin to revert to the second configuration can be selected at the typical human body temperature (i.e., about 36.7° C. or 98° F.) or another temperature. The transition temperature can be selected above the typical human body temperature, and the transition temperature can be achieved in the arms 82 by an application of heat other than from the body. Exemplifying materials for use in the composition of the junction 80 and/or the arms 82 can include nickel-titanium (nitinol), copper-tin, copper-zinc, copper-zinc-tin, copper-zinc-xenon, copper-aluminum-nickel, copper-gold-zinc, gold-cadmium, gold-copper-zinc, iron-beryllium, iron-platinum, indium-thallium, iron-manganese, iron-nickel-titanium-cobalt, nickel-titanium-vanadium, silver-cadmium, and combinations thereof. Exemplifying materials can further include a shape memory polymer, such as polyurethane, polyethylene terephthalate (PET), or high density polyethylene (HDPE).

According to some embodiments, for example as shown in FIG. 4, a heating element 76 can be provided in thermal connection with the junction 80 and the arms 82. The heating element 76 can be connected to the power supply 70 via the first and second leads 72, 74 to direct a current through the heating element 76. The leads 72, 74 can extend alongside the pusher device 78 within a lumen of the positioner 40 and proximally from the heating element 76 to outside the patient's body.

At least a portion of the heating element 76 can provide an electrical circuit with adequate resistance to generate heat while electrical current is applied. The heating element 76 can include a number of coil windings about a portion of the pusher device 78, for example as illustrated in FIG. 4. The heating element 76 can contact or be in close proximity to one or more of the junction 80 and the arms 82. For example, the heating element 76 can be adjacent to or overlap with one or more of the junction 80 and the arms 82. Heat generated by the heating element 76 can be conducted to achieve an increase in temperature along one or more portions of the pusher device 78. Alternatively or in combination, the heating element 76 can include other heat transmission elements such as a heat pipe that transfers heat via convention of heat transfer media therethrough or a fiber optic cable that transfers heat via transmission of light. Alternatively or in combination, the arms 82 and/or the junction 80 may serve as a heating element by directing an electrical current therethrough.

Figure 5A:
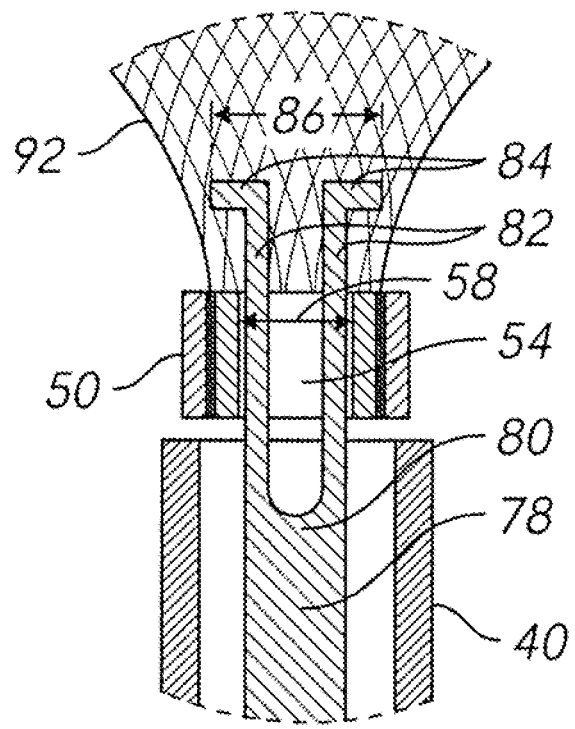
FIG. 5A shows a sectional view of the distal end of the delivery system and proximal portion of the braid ball implant of FIG. 4, in accordance with one or more embodiments of the present disclosure.
Figure 5B:
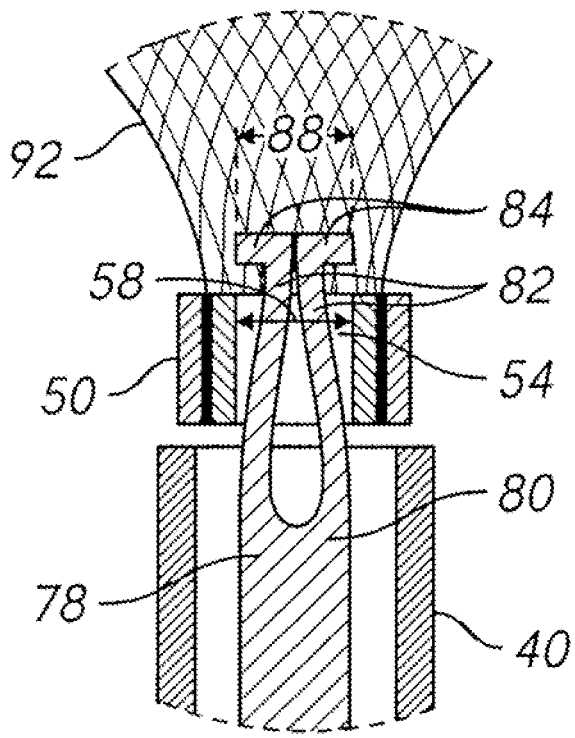
FIG. 5B shows a sectional view of the distal end of the delivery system and proximal portion of the braid ball implant of FIG. 4, in accordance with one or more embodiments of the present disclosure.
Figure 5C:
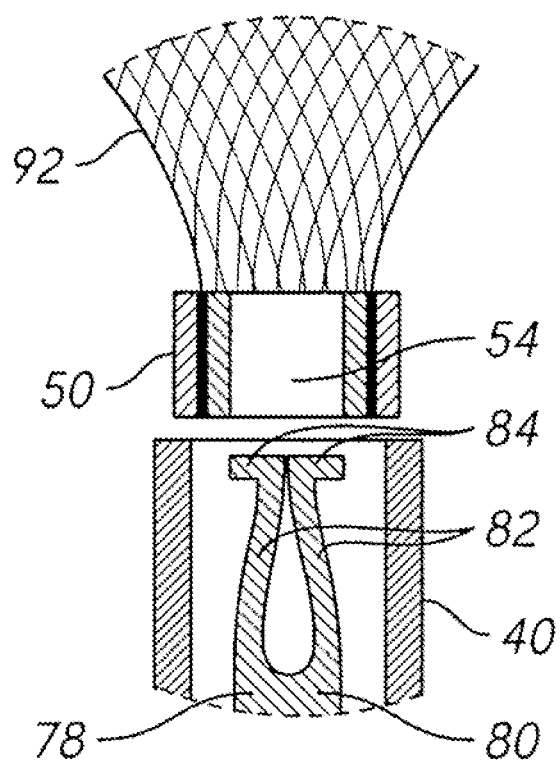
FIG. 5C shows a sectional view of the distal end of the delivery system and proximal portion of the braid ball implant of FIG. 4, in accordance with one or more embodiments of the present disclosure.

FIGS. 5A-5C illustrate various stages of an exemplifying method according to one or more embodiments of the subject technology. FIG. 5A illustrates the delivery connection assembly 12 and implant 95 of FIG. 4 with the hub 50 of the implant held between the pusher device 78 and the positioner 40. FIG. 5B illustrates a stage of detachment in progress. FIG. 5C illustrates the implant 95 detached from the delivery system 10.

According to some embodiments, the implant 95 can be positioned with the positioner 40 and the pusher device 78. Distally directed forces can be transmitted from the positioner 40 to the hub 50 of the implant 95. Additionally, proximally directed forces can be transmitted from the pusher device 78 to the hub 50 of the implant 95.

According to some embodiments, for example as shown in FIGS. 5A and 5B, a transition of the arms 82 can be achieved to facilitate removal of the arms 82 from engagement with the implant 95. The transition can be achieved as described herein, for example by applying heat to the arms 82 and/or the junction 80. As a result of the transition, the distal sections 84 can transition (e.g., move inwardly as illustrated in FIGS. 5A and 5B) from the maximum outer cross-sectional dimension 86 to a second maximum outer cross-sectional dimension 88 that is smaller than the port inner cross-sectional dimension 58.

According to some embodiments, for example as shown in FIGS. 5B and 5C, the transition of the arms 82 (e.g., inward movement of the arms 82) can allow the arms 82 to completely disengage from the implant 95. For example, the arms 82 can move proximally through the port 54 such that the distal sections 84 are entirely proximal of the implant 95. During proximal retraction of the pusher device 78, the positioner 40 can stabilize the implant 95, for example by applying a distally directed force while the positioner 40 contacts the hub 50. Upon full disengagement by the pusher device 78, the pusher device 78, the positioner 40, the microcatheter 14 (if employed), and/or a guide catheter 13 (if employed) can be retracted away from the target implant site and out of the patient, leaving the implant 95 at the target implant site.

Figure 6:
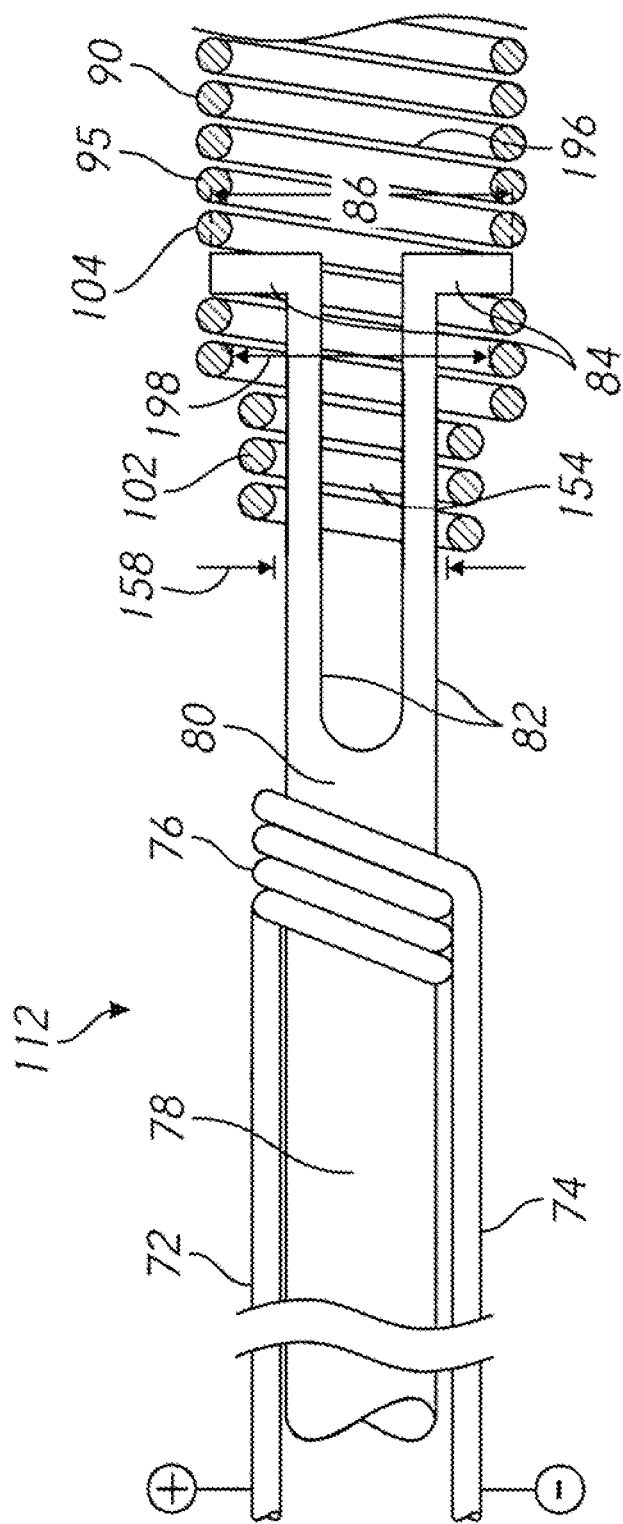
FIG. 6 shows a partial sectional view of a distal end of a delivery system and a proximal portion of a coil implant, in accordance with one or more embodiments of the subject technology.

Although FIGS. 4-5C illustrate an implant 95 comprising a braid ball 92, the delivery system 10 can be used with a coil implant 90, for example as illustrated in part in FIG. 6, according to one or more embodiments of the subject technology. Therefore, the positioner 40 and other elements and components of the delivery system 10 are neither illustrated in FIG. 6 nor described again in detail with reference to FIG. 6, as these components can be readily understood from the other disclosure of them herein.

According to some embodiments, for example as shown in FIG. 6, the pusher device 78 can be configured to engage a coil implant 90. The coil implant 90 can include a proximal portion 102 and a distal portion 104. The proximal portion 102 can be smaller than the distal portion 104 and reside at least partially within a cavity 196 of the distal portion 104, such that the proximal portion 102 and the distal portion 104 at least partially overlap. The proximal portion 102 and the distal portion 104 can form separate portions of a continuous helical coil. Alternatively, the proximal portion 102 and the distal portion 104 can be separate structures that are joined together by an intervening structure. Although FIG. 6 illustrates the proximal portion 102 and the distal portion 104 as coils, the proximal portion 102 and/or the distal portion 104 can also form another circumferentially continuous structure, such as a cylindrical tube as an alternative to a helical coil or in combination with a helical coil.

The proximal portion 102 can be disposed at the proximal end of the distal portion 104 and can further define a port 154. The port 154 can extend completely through the proximal portion 102. The port 154 can be large enough to receive the arms 82 of the pusher device 78. The port 154 can define a port inner cross-sectional dimension 158. The port inner cross-sectional dimension 158 can be a minimum or maximum inner cross-sectional dimension within a region of the proximal portion 102. For example, a region distal to the proximal portion 102 can include a cavity 196 that defines an inner cross-sectional dimension 198 that is greater than the port inner cross-sectional dimension 158.

According to some embodiments, for example as shown in FIG. 6, one or more of the distal sections 84 can be positioned distal to at least a portion of the port 154 and/or within the cavity 196 of the coil implant 90. In at least one configuration, the distal sections 84 can define a maximum outer cross-sectional dimension 86 that is greater than the port inner cross-sectional dimension 158. According to some embodiments, for example as shown in FIG. 6, the distal sections 84 can extend into one or more gaps between windings of the distal portion 104 of the coil implant 90. For example, the distal sections 84 can define a maximum outer cross-sectional dimension 86 that is greater than the inner cross-sectional dimension 198 of the distal portion 104. Accordingly, passage of the distal sections 84 proximally through the port 154 is resisted until the distal sections 84 are transitioned to a different configuration.

Figure 7:
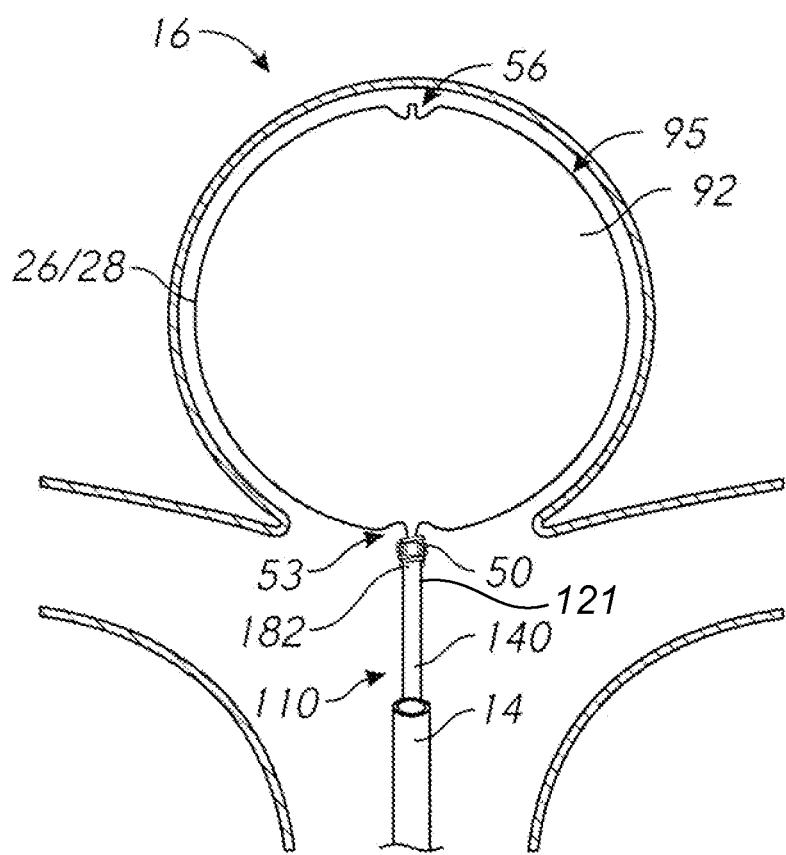
FIG. 7 shows a view of a delivery system in partial cross-section and the braid ball implant of FIGS. 2A-2B, in accordance with some embodiments of the subject technology.

Although FIGS. 3-6 illustrate the delivery system 10 engaging the implant 95 within a cavity thereof, a delivery system 110 can be used to engage an outer portion of the implant 95, for example as illustrated in part in FIG. 7, according to one or more embodiments of the subject technology. Referring now to FIG. 7, the implant 95 can be attached to a distal end 121 of the delivery system 110, and positioned within an aneurysm 16. As illustrated in FIG. 7, the delivery system 110 can comprise a microcatheter 14 and a delivery connection assembly that includes the positioner 140. The microcatheter 14 is advanced until its distal end is in the vicinity of a target site, such as the aneurysm 16, for example as shown in FIG. 7. The positioner 140 is advanced within the catheter 14 to access the target site.

Figure 8A:
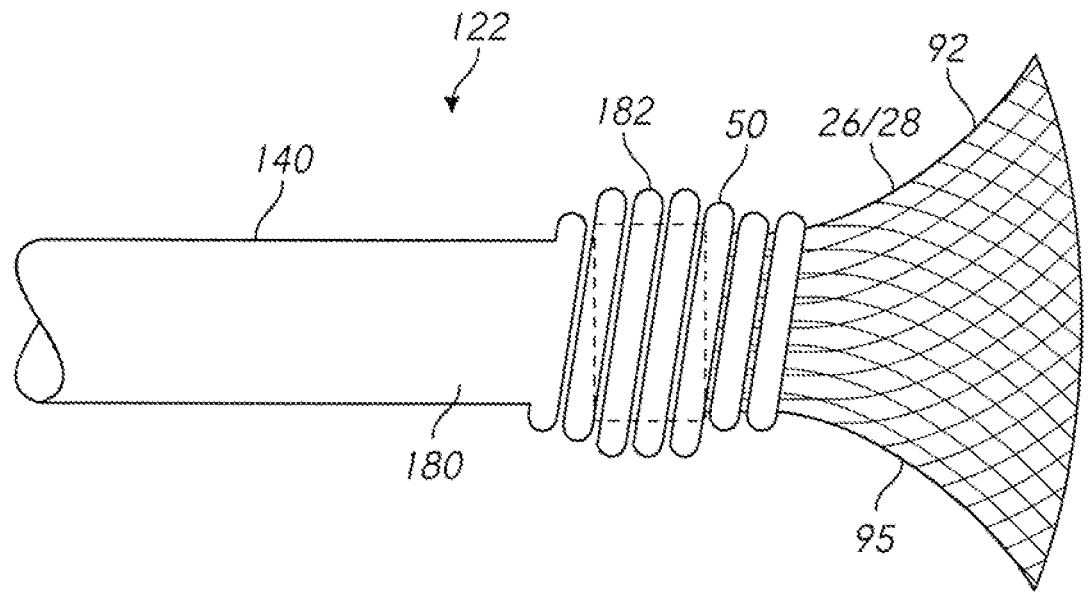
FIG. 8A shows a side view of a distal end of a delivery system and a proximal portion of an implant, in accordance with one or more embodiments of the subject technology.
Figure 8B:
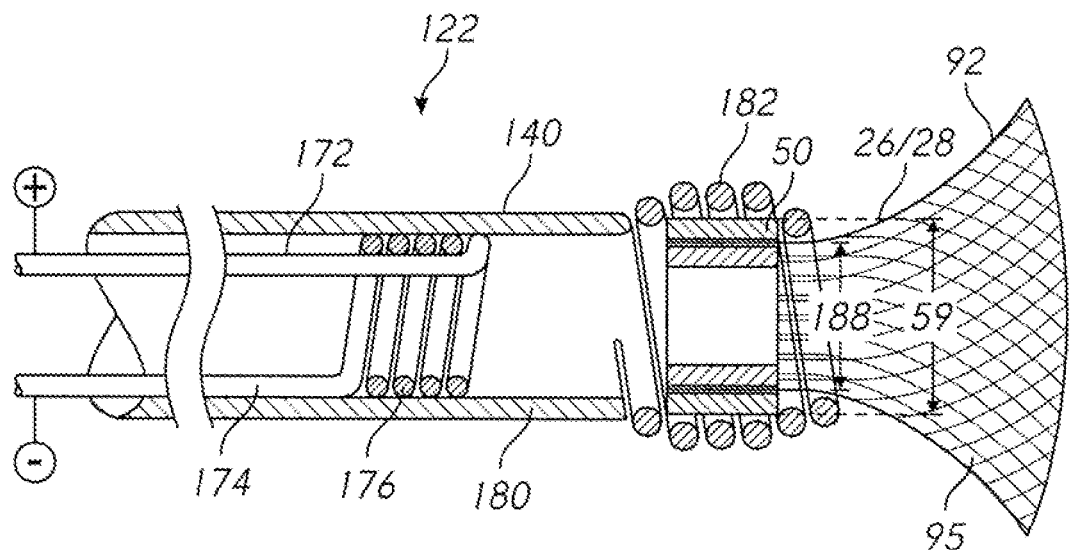
FIG. 8B shows a partial sectional view of the distal end of the delivery system and proximal portion of the implant of FIG. 8A, in accordance with one or more embodiments of the subject technology.

FIG. 8A shows an enlarged view of the distal end 121 of the delivery system 110 and a proximal portion of the implant 95 of FIG. 7. FIG. 8B shows a partial sectional view of the distal end 121 of the delivery system 110 and the proximal portion of the implant 95 shown in FIG. 8. FIGS. 8A and 8B show the implant 95 supported during delivery by a delivery connection assembly 122, from which the implant 95 can also be detached. The delivery connection assembly 122 can include fewer components than the delivery connection assembly 12, described above. According to some embodiments, for example as shown in FIGS. 8A and 8B, the delivery connection assembly 122 can include the positioner 140 and one or more coils 182 extending helically and distally from a pusher section 180 of the positioner 140.

The coil 182 can be positioned to extend about an outer periphery of a portion of the implant 95. For example, the coil 182 can wrap up around and engage the hub 50 of the implant 95. The coil 182 can extend proximal to the hub 50, along a length of the hub 50, and/or distal to the hub 50. For example, the coil 182 can extend to regions on one or both sides of the hub 50. A distalmost region of the coil 182 can engage a distal end of the hub 50. A proximalmost region of the coil 182 can engage a proximal end of the hub 50. Alternatively, a separate structure of the delivery connection assembly 122, e.g., a stop, can engage a proximal end of the hub 50.

The coil 182 can be affixed to the pusher section 180 of the positioner 140, such that movement of the pusher section 180 substantially transmit forces to the coil 182 and the implant 95. In at least one configuration, the coil 182 can be biased to form an inner cross-sectional dimension 188 that is smaller than the hub outer cross-sectional dimension 59. The bias of the coil 182 can refer to the tendency of the coil 182, in a relaxed configuration, to naturally move to a shape in which it forms the inner cross-sectional dimension 188. Despite this bias, the coil 182 may be prevented from completely achieving the shape of the relaxed configuration and instead engage the hub 50. While engaged on the hub 50, at least a portion of the coil 182 may have an inner cross-sectional dimension 188 that is equal to the hub outer cross-sectional dimension 59 of the hub 50. The bias can provide a force of engagement with the hub 50. Accordingly, movement of the hub 50 is limited or resisted until the coil 182 is transitioned to a different configuration.

According to some embodiments, the coil 182 is configured to flex, bend, unwind, and/or radially expand. Such action can be achieved based on a programmed characteristic of the coil 182. When the coil 182 is at or above a transition temperature, the coil 182 can transition to a second configuration, such as an austenite state in a shape memory alloy, in which the coil 182 in a relaxed state can disengage from the implant 95, as will be more fully described herein.

The transition temperature at which the coil 182 begins to revert to the second configuration can be selected at the typical human body temperature (i.e., about 36.7° C. or 98° F.) or another temperature. The transition temperature can be selected above the typical human body temperature, and the transition temperature can be achieved in the coil 182 by an application of heat other than from the patient's body. Exemplifying materials for use in the composition of the coil 182 can include nickel-titanium (nitinol), copper-tin, copper-zinc, copper-zinc-tin, copper-zinc-xenon, copper-aluminum-nickel, copper-gold-zinc, gold-cadmium, gold-copper-zinc, iron-beryllium, iron-platinum, indium-thallium, iron-manganese, iron-nickel-titanium-cobalt, nickel-titanium-vanadium, silver-cadmium, and combinations thereof. Exemplifying materials can further include a shape memory polymer, such as polyurethane, polyethylene terephthalate (PET), or high density polyethylene (HDPE).

According to some embodiments, for example as shown in FIG. 8B, a heating element 176 can be provided in thermal connection with the pusher section 180 and the coil 182. The heating element 176 can be connected to the power supply 70 via the first and second leads 172, 174 to direct a current through the heating element 176. The leads 172, 174 can extend within a lumen of the positioner 140 and proximally from the heating element 176 to outside the patient's body.

At least a portion of the heating element 176 can provide an electrical circuit with adequate resistance to generate heat while electrical current is applied. The heating element 176 can include a number of coil windings within a portion of the positioner 140, for example as illustrated in FIG. 8B. The heating element 176 can contact or be in close proximity to one or more of the pusher section 180 and the coil 182. For example, the heating element 176 can be adjacent to or overlap with one or more of the pusher section 180 and the coil 182. Heat generated by the heating element 176 can be conducted to achieve an increase in temperature along one or more portions of the positioner 140. Alternatively or in combination, the heating element 176 can include other heat transmission elements such as a heat pipe that transfers heat via convention of heat transfer media therethrough or a fiber optic cable that transfers heat via transmission of light. Alternatively or in combination, the coil 182 and/or the pusher section 180 may serve as a heating element by directing an electrical current therethrough.

While the coil 182 can be a single filament helical winding, as shown in FIGS. 8A and 8B, other shapes for engaging the implant 95 are contemplated. According to some embodiments, the coil 182 can include multiple filaments that are the same or different sizes. The filaments can be wound in the same direction or counter wound. The filaments can be provided in a single layer or in multiple concentric layers. Alternatively or in combination, other shapes can be used to engage the implant 95, such as a circumferentially continuous structure, such as a cylindrical tube.

Figure 9A:
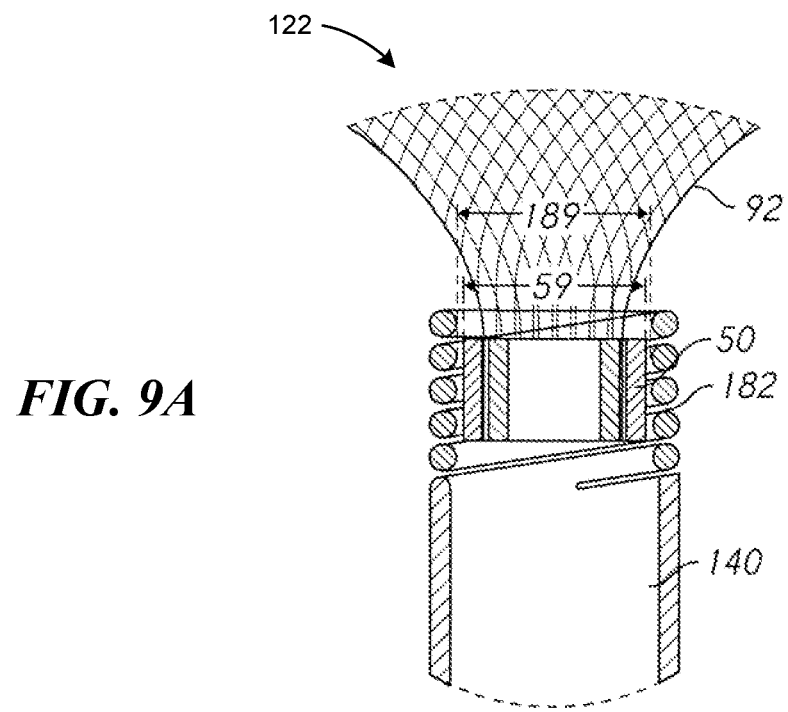
FIG. 9A shows a sectional view of the distal end of the delivery system and the proximal portion of the implant of FIG. 8A, in accordance with one or more embodiments of the present disclosure.
Figure 9B:
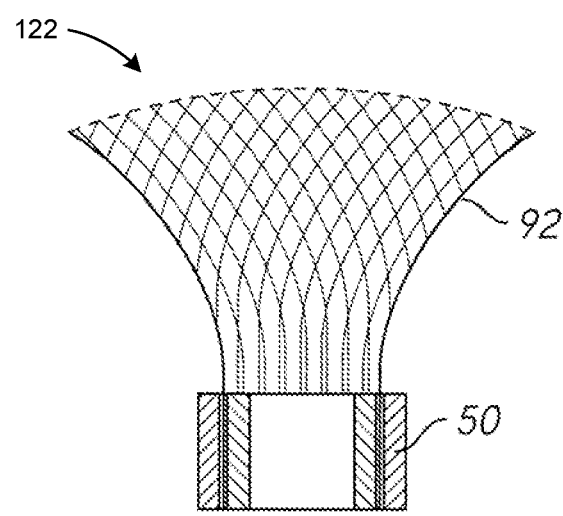
FIG. 9B shows a sectional view of the distal end of the delivery system and the proximal portion of the implant of FIG. 8A, in accordance with one or more embodiments of the present disclosure.
Figure 9B:
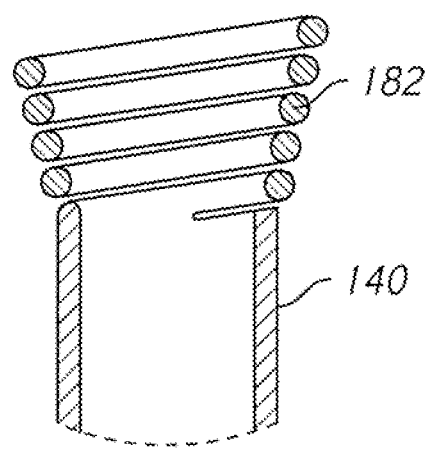

FIGS. 9A and 9B illustrate various stages of an exemplifying method according to one or more embodiments of the subject technology. FIG. 9B illustrates the delivery connection assembly 122 and implant 95 of FIG. 8B with the hub 50 of the implant 95 held within the coil 182. FIG. 9B illustrates a stage of detachment in progress. FIG. 9B illustrates the implant 95 detached from the delivery connection assembly 122.

According to some embodiments, the implant 95 can be positioned with the delivery connection assembly 122. While the hub 50 is held within the coil 182, distally and/or proximally directed forces can be transmitted from the positioner 140 to the hub 50 of the implant 95. According to some embodiments, for example as shown in FIGS. 9A and 9B, a transition of the coil 182 can be achieved to facilitate removal of the coil 182 from engagement with the implant 95. The transition can be achieved as described herein, for example by applying heat to the coil 182 and/or the pusher section 180. As a result of the transition, the coil 182 can transition from (or from a bias toward) the inner cross-sectional dimension 188 to a second inner cross-sectional dimension 189 that is larger than the hub outer cross-sectional dimension 59 of the hub 50. The inner cross-sectional dimension 188 and the second inner cross-sectional dimension 189 can occur at the same region of the coil 182 at different stages of deployment.

According to some embodiments, for example as shown in FIGS. 9A and 9B, a transition of the coil 182 can allow the coil 182 to completely disengage from the implant 95. For example, the coil 182 can move proximally and entirely off of the hub 50. Upon full disengagement by the positioner 140, the positioner 140, the microcatheter 14, and/or the guide catheter 13 can be retracted away from the target implant site and out of the patient, leaving the implant 95 at the target implant site.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A delivery system, comprising:
   an implant comprising a proximal portion including a circumferentially continuous hub that defines a hub lumen extending therethrough, the hub defining an outer cross-sectional dimension; and
   a pusher device comprising:
      tubular member defining a tubular membrane lumen;
      a coil couple to a distal end portion of the tubular membrane, the coil extending helically about the implant proximal portion;
      a heating element disposed within the tubular member lumen at a position proximal to the coil; and
      first and second conductive leads electrically coupled to the heating element and extending proximally through the tubular member lumen for electrical connection to an extracorporeal power supply;
   wherein the pusher device is configured such that heat from the heating element conducts along the tubular membrane to the coil;
   wherein the coil has a first configuration in which the coil is biased to form a coil lumen with a first inner cross-sectional dimension, smaller than the outer cross-sectional dimension of the proximal portion, wherein when the coil engages the proximal portion of the implant, the coil lumen is in fluid communication with the hub lumen;
   wherein the coil has a second configuration in which the coil lumen has a second inner cross-sectional dimension, larger than the outer cross-sectional dimension of the proximal portion; and
   wherein the coil is configured to transition from the first configuration to the second configuration when above a transition temperature.

2. The delivery system of claim 1, wherein at least a portion of the coil extends distally of an entire length of the proximal portion.

3. The delivery system of claim 1, wherein the coil is of a shape memory material.

4. The delivery system of claim 1, wherein the heating element is spaced apart from the coil.

5. The delivery system of claim 1, wherein the heating element comprises a plurality of coil windings disposed within the tubular member lumen.

6. A delivery system, comprising:
   an implant comprising a proximal portion including a circumferentially continuous hub that defines a hub lumen extending therethrough, the hub defining an outer cross-sectional dimension; and
   a positioner comprising a tubular member defining a positioner lumen and a distally located radially expandable member defining an expandable member lumen, the radially expandable member being configured to transition from a first configuration to a second configuration in response to a temperature change, wherein in the first configuration the expandable member lumen has a first cross-sectional dimension that is smaller than the outer cross-sectional dimension of the implant proximal portion, and wherein in the second configuration the expandable member lumen has a second cross-sectional dimension that is greater than the outer cross-sectional dimension of the implant proximal portion; and
   a heating element disposed within the positioner lumen and configured such that heat from the heating element conducts along the tubular member to the radially expandable member,
   wherein when the expandable member engages the proximal portion of the implant, the expandable member lumen is in fluid communication with the hub lumen.

7. The delivery system of claim 6, wherein the radially expandable member surrounds at least a portion of the proximal portion of the implant when the expandable member engages the proximal portion of the implant.

8. The delivery system of claim 6, wherein the radially expandable member comprises a coil surrounding at least a portion of the proximal portion of the implant.

9. The delivery system of claim 6, wherein the radially expandable member comprises a shape memory material.

10. The delivery system of claim 6, wherein at least a portion of the radially expandable member extends distally of an entire length of the proximal portion.

11. The delivery system of claim 6, wherein the heating element is spaced apart from the radially expandable member.

12. The delivery system of claim 6, wherein the heating element comprises a plurality of coil windings disposed within the positioner lumen.

13. A method of delivering an implant, the method comprising:
   positioning the implant at a target location within a patient while the implant is attached to a pusher device, wherein the implant comprises a proximal portion including a circumferentially continuous hub that defines a hub lumen extending therethrough, the hub defining an outer cross-sectional dimension, wherein the pusher device comprises a tubular member coupled to a coil having a coil lumen and extending helically about the proximal portion such that the coil lumen is in fluid communication with the hub lumen, the pusher device further comprises a heating element disposed within a tubular member lumen at a position spaced apart from the coil; and
   releasing the implant from the pusher device by heating the heating element, causing heat to conduct along the tubular member to the coil, thereby increasing a temperature of the coil, such that the coil transitions from (i) a first configuration in which the coil is biased to form the coil lumen with a first inner cross-sectional dimension, smaller than the outer cross-sectional dimension of the proximal portion to (ii) a second configuration in which the coil lumen has a second inner cross-sectional dimension, larger than the outer cross-sectional dimension of the proximal portion.

14. The method of claim 13, wherein the releasing comprises retracting the coil proximally from the implant.

15. The method of claim 13, wherein the heating element is spaced apart from the coil.

16. The method of claim 13, wherein the heating element comprises a plurality of coil windings disposed within the tubular member lumen.

* * * * *